US00PP23071P3

(12) United States Plant Patent
Dirr

(10) Patent No.: US PP23,071 P3
(45) Date of Patent: Sep. 25, 2012

(54) ***LAGERSTROEMIA* PLANT NAMED 'PIILAG-II'**

(50) Latin Name: ***Lagerstroemia* L.**
Varietal Denomination: PIILAG-II

(75) Inventor: Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 282 days.

(21) Appl. No.: 12/802,192

(22) Filed: Jun. 1, 2010

(65) Prior Publication Data

US 2011/0296570 P1 Dec. 1, 2011

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

PP16,917 P2 8/2006 Dirr

OTHER PUBLICATIONS

Plant Introductions, Inc.—page showing color pictures of *Lagerstroemia* selections, (including PIILAG-II) from booklet distributed at trade shows and to nurseries since Jan. 2010.

*Primary Examiner* — Wendy C Haas
(74) *Attorney, Agent, or Firm* — Greenlee Sullivan P.C.

(57) ABSTRACT

A new and distinct cultivar of *Lagerstroemia* plant named 'PIILAG-II', characterized by its compact, rounded growth habit, reddish new growth and dark green foliage in summer, neon-rose flowers, and resistance to powdery mildew and *Cercospora* leaf spot.

3 Drawing Sheets

Genus and species of plant claimed: *Lagerstroemia* L.
Variety denomination: 'PIILAG-II'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'PIILAG-II'.

The new *Lagerstroemia* plant originated in 2006 from open-pollinated seed of 'Gamad I' (U.S. Plant Pat. No. 16,917). The cultivar 'PIILAG-II' originated and was discovered in a cultivated environment in Dearing, Ga.

Asexual reproduction of the new cultivar since 2007 by stem cuttings in Watkinsville, Ga. has shown that all the unique features of this new *Lagerstroemia*, as herein described, are stable and reproduced true-to-type through successive generations of such asexual propagation.

SUMMARY OF THE INVENTION

Plants of the new cultivar 'PIILAG-II' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-II'. These characteristics in combination distinguish 'PIILAG-II' as a new and distinct cultivar: 1. Compact, rounded growth habit; 2. Reddish new growth and dark green foliage in summer; 3. Neon-rose flowers; 4. Resistance to powdery mildew and *Cercospora* leaf spot.

Plants of the new *Lagerstroemia* 'PIILAG-II' differ from plants of the parent, 'Gamad I', primarily in flower color and growth habit, as plants of 'Gamad I' have cherry red flowers, and an overall tighter and more compact growth habit, whereas plants of 'PIILAG-II' have neon-rose flowers and an overall larger and looser growth habit.

BRIEF DESCRIPTION OF THE DRAWINGS

The accompanying color photographs illustrate the flower and foliage characteristics and the overall appearance of the new *Lagerstroemia*, showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
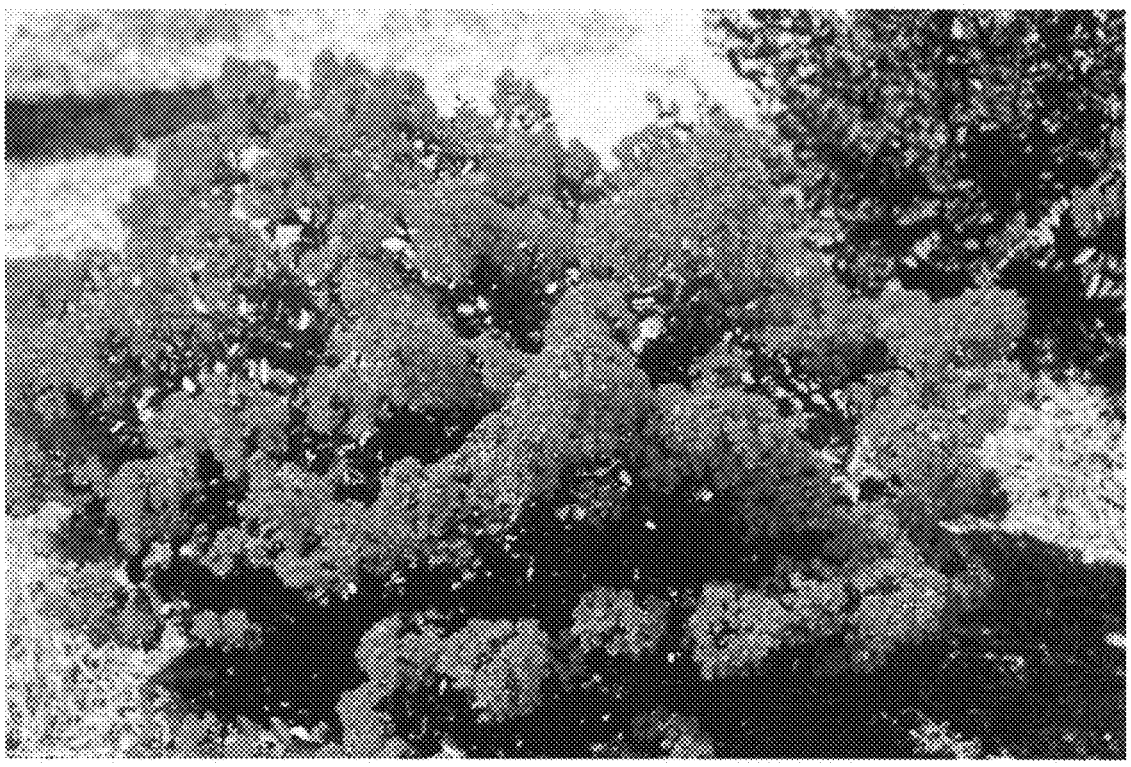
FIG. 1 illustrates the overall appearance of a mature plant of 'PIILAG-II'.
Figure 2:
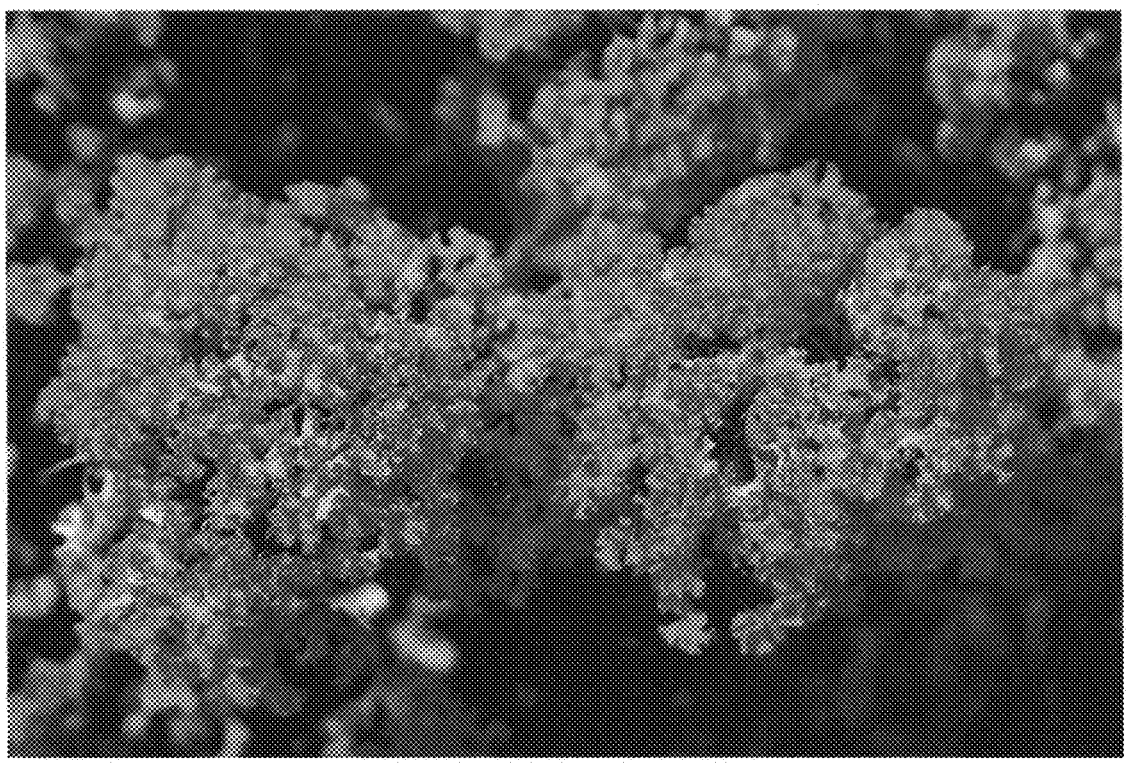
FIG. 2 illustrates a close-up view of the inflorescences of 'PIILAG-II'.
Figure 3:
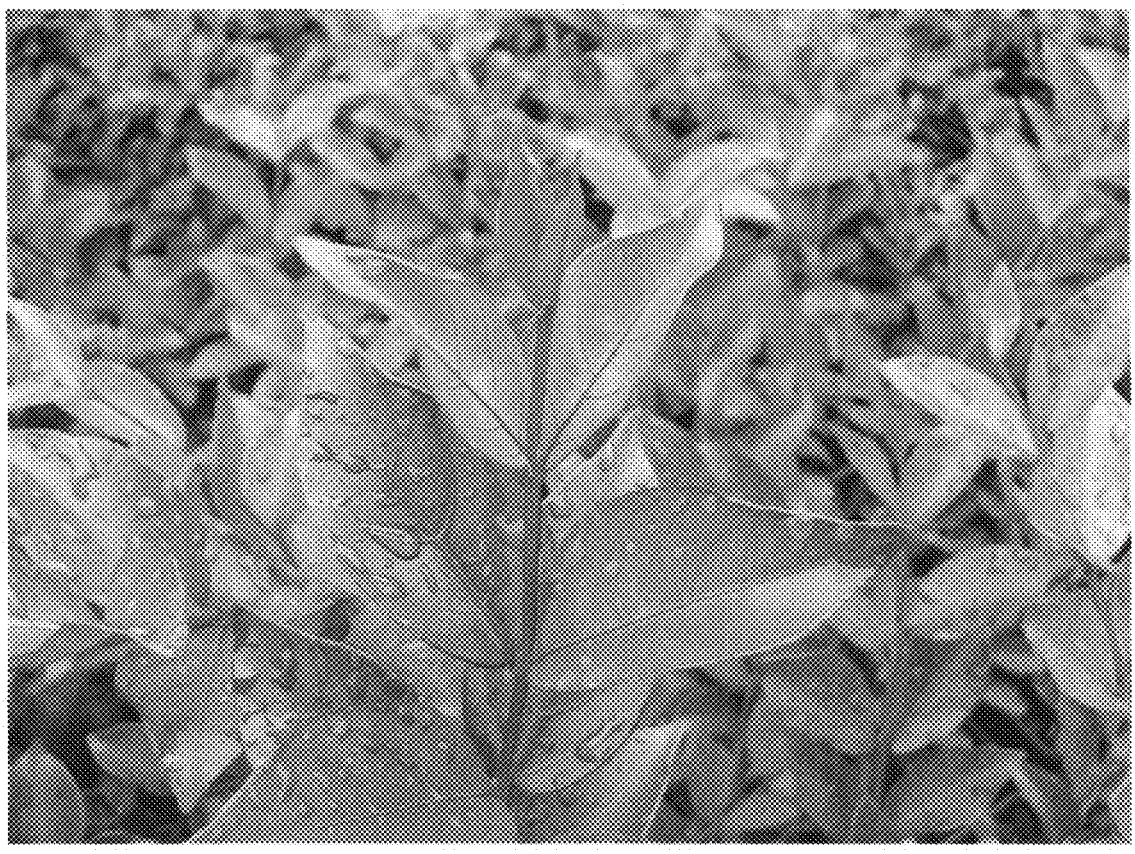
FIG. 3 illustrates a close-up view of the new growth of 'PIILAG-II'.

In the following description, color references are made to The Royal Horticultural Society Colour Chart, 2001 Edition, except where general terms of ordinary dictionary significance are used. Plants used for the description were approximately 2 and a half years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-II'.

Parentage:

*Female, or seed, parent.*—*Lagerstroemia* 'Gamad I'.

*Male, or pollen, parent.*—Unknown (open-pollinated).

Propagation:

*Type cutting.*—Terminal cuttings.

*Time to initiate roots, summer.*—About 21 days at 32 C°.

Plant description: Flowering shrub; compact, rounded growth habit. Freely branching; pruning enhances lateral branch development.

*Root description.*—Numerous, fine, fibrous and well-branched.

*Plant size.*—The original plant, now about 4-years-old in the ground, is about 90 cm in height from the soil level to the top of the inflorescences, and about 90 cm in diameter. First year stems have a diameter of about 2.5 mm. Shape: squarish. Second year and older stems have a diameter of about 5 mm or more. Shape: round.

*Trunk diameter.*—About 1.8 cm at the soil line. Color: close to 199C.

*Internode length.*—About 1.5 cm.

*Strength.*—Flexible when young, easily broken once mature.

*First year stem color* (*young*).—Close to 176B. Color (woody): close to 199B.

*Second year and older stem color.*—Close to 199B.

*Bark.*—Exfoliates in strips beginning on second or third year stems.

Vegetative buds: Sub-opposite to alternate in arrangement, imbricate, conical, with no pubescence.

*Color.*—Close to 178A.

*Size.*—About 3 mm in length and 2 mm in width.

Foliage description:

*Arrangement.*—Sub-opposite to alternate, simple.

*Length.*—About 4 cm.

*Width.*—About 2.5 cm.

*Shape.*—Elliptical.

*Apex.*—Acute.

*Base.*—Cuneate.

*Margin.*—Entire.

*Texture* (*upper and lower surfaces*).—Glabrous.

*Venation pattern.*—Pinnate.

*Venation color in developing foliage* (*upper and lower surfaces*).—178B.

*Venation color in fully expanded foliage* (*upper surface*).—Close to 146B.

*Venation color in fully expanded foliage* (*lower surface*).—Close to 146D.

*Color in developing foliage* (*upper surface*).—Close to 178B.

*Color in developing foliage* (*lower surface*).—Close to 178B.

*Color in fully expanded foliage* (*upper surface*).—Close to 147A.

*Color in fully expanded foliage* (*lower surface*).—Close to 146B.

*Color of leaf margin in developing foliage* (*upper and lower surfaces*).—178B.

*Color of leaf margin in fully expanded foliage* (*upper and lower surfaces*).—Ranges from 178D to 146B.

*Fall color.*—Can be 172C, 178C, or any combination of these colors.

*Petiole length.*—About 1 mm.

*Petiole diameter.*—About 1 mm.

*Petiole color.*—Close to 146B.

Flower description: Flowers are produced from about June to September in Watkinsville, Ga. An inflorescence is showy for about two weeks, and individual flowers last about one day and are self-cleaning.

*Inflorescence type.*—Panicle.

*Inflorescence length.*—About 8.5 cm.

*Inflorescence width.*—About 9.5 cm.

*Peduncle.*—About 7 cm in length, about 2 mm in diameter, color is close to 178A, and no pubescence.

*Individual flowers.*—About 2 cm by 4 cm.

*Flower buds.*—Length: about 6 mm; Diameter: about 6 mm; Color: close to 145C, maturing close to 181B.

*Pedicels.*—About 1 cm in length, close to 178A in color, and no pubescence.

*Calyx.*—About 8 mm in length, about 7 mm in diameter, color close to 53C, and no pubescence.

Petals:

*Arrangement/appearance.*—Usually 6 per flower.

*Petal length.*—About 2 cm.

*Petal width.*—About 1.2 cm.

*Petal shape.*—Fan-shaped.

*Petal apex.*—Ruffled, rounded.

*Petal base.*—Sagittate.

*Petal margin.*—Ruffled.

*Petal color.*—Upper and lower surfaces are close to N57A.

Stamens:

*Quantity/arrangement.*—About 20 to 25 short stamens clustered in the center, about 7 mm long, filament color is close to 1D, and anther color is close to 14A. The short stamens are surrounded by 6 longer stamens, about 1.5 cm long. Filament color is close to 50B, and anther color is close to 14A. The stamens are not pubescent.

*Pollen.*—Produced in moderate quantities and is close to 145C in color.

Pistils:

*Quantity.*—One superior pistil per flower.

*Pubescence.*—None.

*Pistil length.*—About 1.5 cm in length.

*Stigma shape.*—Round, about 1 mm in diameter.

*Stigma color.*—Close to 148A.

*Style color.*—Close to 181A and about 1 cm in length.

*Ovary color.*—Close to 10B and about 2 mm in diameter.

Fruit:

*Type/appearance.*—Six-valved, dehiscent, broad ellipsoidal capsule.

*Length.*—About 8 mm.

*Diameter.*—About 6 mm.

*Mature color.*—Close to 200C. Each capsule contains multiple seeds that are about 5 mm long, 3 mm wide, and close to 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG-II', as illustrated and described herein.

* * * * *